United States Patent [19]

Hamprecht

[11] Patent Number: 4,582,898
[45] Date of Patent: Apr. 15, 1986

[54] AZO DYESTUFFS FROM CYANO-AMINO-BENZISOTHIAZOLES

[75] Inventor: Rainer Hamprecht, Odenthal, Fed. Rep. of Germany

[73] Assignee: Bayer Aktiengesellschaft, Leverkusen, Fed. Rep. of Germany

[21] Appl. No.: 660,337

[22] Filed: Oct. 12, 1984

Related U.S. Application Data

[62] Division of Ser. No. 492,075, May 6, 1983, abandoned.

[30] Foreign Application Priority Data

May 28, 1984 [DE] Fed. Rep. of Germany ..... 32201176

[51] Int. Cl.⁴ .................. C09B 29/042; C09B 29/09; C09B 29/44; D06P 1/18
[52] U.S. Cl. .................................. 534/788; 558/413; 558/416; 534/590; 558/419; 534/727; 534/733; 534/768; 534/778; 548/212
[58] Field of Search ............... 534/788, 768, 778, 727, 534/733

[56] References Cited

U.S. PATENT DOCUMENTS 3,507,903  4/1970  Gottschlich et al. .......... 260/465 E
3,573,273  3/1971  Seefelder et al. .................... 534/788
4,292,239  9/1981  Kruckenberg et al. ............. 534/788

FOREIGN PATENT DOCUMENTS 1543620  7/1969  Fed. Rep. of Germany ... 260/465 E
2617807  11/1977  Fed. Rep. of Germany ... 260/465 R

OTHER PUBLICATIONS

Imperial I, Chemical Abstracts, vol. 86, #141617u, (1977).
Imperial II, Chemical Abstracts, vol. 88, #38943q, (1978).
Gewald et al., Chemical Abstracts, vol. 95, 8/31/81, No. 9, p. 753.
Rigert et al., Chemical Abstracts, vol. 83, 9/29/75, No. 13, pp. 507–508.

Primary Examiner—Floyd D. Higel
Attorney, Agent, or Firm—Sprung, Horn, Kramer & Woods

[57] ABSTRACT

Aniline derivatives of the formula

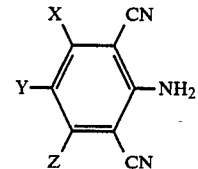

wherein
X=alkyl,
Z=H or alkyl, and
Y=S-alkyl, $SO_2$-alkyl, $CO_2$-R (R=alkyl, cycloalkyl, or H) or—if Z=H—Br, are diazo components for preparing valuable azo dyestuffs and starting materials for preparing compounds of the formula

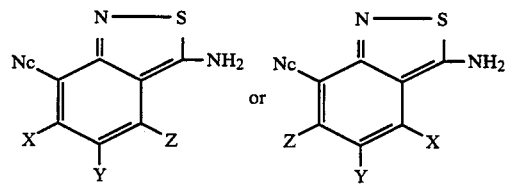

(VIa)     (VIb)

and new azo dyestuffs derived therefrom and which—in their nonionic form—are highly suitable for dyeing polyester fibres in blue shades having high tinctorial strength and high fastness levels.

5 Claims, No Drawings

AZO DYESTUFFS FROM CYANO-AMINO-BENZISOTHIAZOLES

This is a division of application Ser. No. 492,075, filed May 6, 1983, now abandoned.

The invention relates to aniline derivatives of the formula

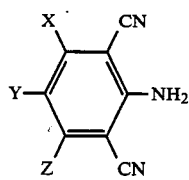
(I)

wherein
X denotes alkyl,
Y denotes —S—alkyl, —SO$_2$-alkyl, —CO$_2$—R, or — if Z=H—bromine, and
Z denotes hydrogen or alkyl,
where
R represents alkyl, cycloalkyl, or hydrogen, and the alkyl radicals have 1-6, preferably 1-4, C atoms, and the cycloalkyl radicals have 5 or 6 ring C atoms, and to their preparation and use for preparing amono-benzisothiazoles and azo dyestuffs derived therefrom.

Particularly preferable alkyl radicals are methyl and — in the case of the carboxylate—ethyl. Cyclohexyl is the preferred cycloalkyl radical.

Preferable aniline derivatives have the formula I wherein
X denotes methyl, and
Z denotes hydrogen.

Very particularly preferable compounds have the formula I wherein
X and Z have the abovementioned general and particular meanings, and
Y represents —CO$_2$—C$_1$-C$_6$-alkyl.

While 2,6-dicyanoanilines having a nitro, bromine or alkyl substituent in the 4-position, an alkyl radical in the 3/5-position, or an alkylmercapto radical in the 3-position are known (compare British Patent Specification No. 1,127,085, German Offenlegungsschrift No. 1,644,177, German Offenlegungsschrift No. 2,605,622, German Offenlegungsschrift No. 2,137,719, German Offenlegungsschrift No. 2,340,569 and in East German Patent Specification No. 142,542), compounds of the formula I have hitherto not been described in the literature.

It has now been found that the new aniline derivatives are obtained in a simple manner when compounds of the formula

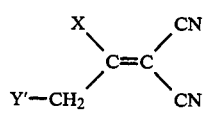
(II)

wherein
Y' represents S-alkyl or —CO$_2$R,
are condensed with compounds of the formula

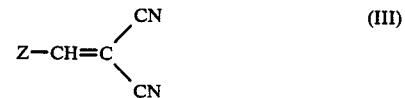

and the product is aromatised, both steps being carried out in a way which is in itself known, and, if appropriate, in the reaction product the radical S-alkyl is oxidised to the corresponding alkylsulphonyl radical or the radical COOR is hydrolysed to the carboxylic acid radical, which is replaced by a bromine substituent by reaction with bromine.

Those of the starting materials II and III which are not known can be prepared by methods which are in themselves known (compare J. pr. Chem. 313, 678 (1971), Bl. chem. Soc. Japan 2, 306 (1927) and German Offenlegungsschrift No. 2,340,569).

II is condensed with III by means of base catalysis in the presence of an organic solvent at temperatures of −10° to 40° C., preferably of −5° to 25° C.

Suitable base catalysts are alkali metal or alkaline earth metal alcoholates and, preferably, secondary amines, such as diethylamine, morpholine, piperidine or N-methylaniline.

These catalysts can be used in up to molar amounts (relative to II and III).

Suitable solvents are alcohols, such as methanol, ethanol, or propanol, and dipolar aprotic solvents, such as acetonitrile or dimethylformamide.

In most cases the abovementioned conditions for the condensation also suffice for the aromatisation. If not, brief reheating, advantageously at the boiling point of the solvent, is necessary.

Conventional methods are used to oxidise the compounds where Y=S-alkyl and to hydrolyse compounds where Y=COOR. The carboxylic acid is brominated in, for example, a solution in hydrochloric acid.

The new aniline derivatives are obtained in a particularly favourable way when the synthesis is designed as a one-vessel reaction, by reacting a mixture of (a) 1 equivalent of a compound of the formula

(b) 1 equivalent of a compound of the formula

and
(c) 2 equivalents of malodinitrile in the presence of a base.

Preferably 1 equivalent of the base (for example morpholine) is added at 0° C. and the reaction completed by stirring at room temperature. In exceptional cases it is necessary to heat up to temperatures of 60°-100° C.

Although a large number of the new aniline derivatives (I) are prepared using methods which are in themselves known, the smooth course of the reaction must be termed surprising, since, for example, the occurrence of secondary reactions, due to the use of the ester substituent Y=CO$_2$R, could not be precluded (compare pyridone formation in accordance with Austr. J. Chem. 28, 581 (1975)).

The new aniline derivatives (I) can be used for many purposes, and are for example suitable for preparing valuable azo dyestuffs by means of direct diazotisation and subsequent coupling onto suitable coupling components.

However, particularly interesting dyestuffs are obtained when anilines of the formula I are converted by the addition of H₂S (to give the monothioamide) and subsequent oxidative ring closure into aminobenzisothiazoles of the formula (VIa)    (VIb)

which are diazotised and coupled.

This method of preparing the aminobenzothiazoles (VI) is in itself known (compare German Auslegeschrift No. 1,544,375=British Patent Specification No. 1,112,146, German Offenlegungsschrift No. 2,412,975=British Patent Specification No. 1,493,037, German Offenlegungsschrift No. 1,644,169, and German Offenlegungsschrift No. 2,617,807).

Depending on the substitution pattern of the anilines (I) used as starting materials, compounds VIa or VIb, or mixtures of the two, are formed.

The situation is different when preferable compounds of the formula I, in which Z=H, are used, it being highly probable that the VIa isomer is exclusively formed.

Compounds of the formula VI in which Y=SO₂-alkyl can also be prepared by subsequently oxidising compounds of the formula in which Y=S-alkyl, which oxidation, to give the sulphone, can, if desired, be carried out as a one-vessel reaction together with the oxidative ring closure.

Any azo dyestuff derived from the aminobenzisothiazoles VI is new and also a subject of this invention. They are of the formula (VIIa)

or (VIIb)

wherein
K represents the radical of a coupling component, and the remaining radicals have the abovementioned meaning.

Preferable dyestuffs of the formula VII are disperse dyestuffs. They are of the formula (VIII)

wherein
K' represents a sulpho-free coupling component of the aminobenzene or aminonaphthalene series, and
X and Y have the abovementioned general and specific meanings.

Particularly preferable dyestuffs have the formula VIII
wherein
K' represents a radical of the formula wherein
$R_1$ denotes hydrogen, —CH₃, Cl, CF₃, or, preferably, —NH—W, W denotes —COH, —CO-alkyl, —CO-aryl, —CO₂-alkyl, —CO₂-aryl, —SO₂-alkyl, —SO₂-aryl or —PO(O-alkyl)₂

$R_2$ denotes hydrogen, alkyl, —O-alkyl, O-aryl, Cl or Br, $R_3$ denotes hydrogen, alkyl, aryl, or aralkyl, and $R_4$ denotes hydrogen, alkyl or aralkyl, and the abovementioned alkyl radicals have 1-6, preferably 1-4, C atoms and can be substituted by OH, Cl, —O—C₁-C₄-alkyl, —O-phenyl, CN, —CO₂—C₁-C₄-alkyl or —OCO—NH—C₁-C₄-alkyl, the aryl radicals are phenyl radicals, and the aralkyl radicals are phenyl—C₁-C₃-alkyl radicals which can be substituted by Cl, CH₃, or C₁-C₂-alkoxy, and where the two radicals $R_2$ and $R_4$ can also jointly form a C₃-alkylene chain.

Very particularly preferable dyestuffs have the formula (VIII)
wherein
X denotes CH₃,
Y denotes SCH₃, SO₂CH₃, or — preferably——CO₂C₁-C₂-alkyl,
W₁ denotes —COH, —CO-alkyl, —CO-aryl, —CO₂-alkyl, or —SO₂-alkyl,
$R_2$ denotes hydrogen or —O—C₁-C₄-alkyl, and
$R_3/R_4$ denote hydrogen, C₁-C₆-alkyl or C₁-C₄-alkyl, or —O—C₁-C₆-alkyl.

The new dyestuffs are suitable for dyeing a very wide variety of fibre types. The preferred disperse dyestuffs of the formula VIII have very high tinctorial strength, and are naturally used for dyeing hydrophobic, synthetic fibres, in particular polyester and cellulose ester fibres, on which they produce violet to blue dyeings having high fastness levels.

EXAMPLE 1

Preparation of

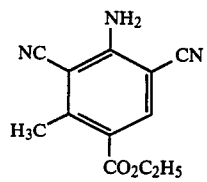

A solution of 37.5 ml of 37 percent strength aqueous formaldehyde in 50 ml of methanol is added dropwise at 0° C., within 30 minutes, to 65 g of ethyl acetate; a solution of 66 g of malodinitrile in 50 ml of methanol is then added dropwise at 0° C. The mixture is stirred for 30 minutes, and a solution of 43.3 ml of morpholine in 50 ml of methanol is then added at 0° C. in the course of 2.5 hours. The mixture is stirred at 0° C. for 12 hours and at room temperature for 48 hours. The solids are filtered off with suction and washed with a small amount of methanol. Yield: 50.5 g. The mother liquor is refluxed for 12 hours and seeded with crystals, thereby giving a further 4.6 g of product.

Melting point: 149° C.
$m_e+$: 229.
1H-N.M.R. (DMSO-$d_6$/TMS): $\delta$ = 1.35 (t, 3H); 2.65 (s, 3H); 4.26 (q, 2H); 7.17 (s, 2H); 8.02 (s, 1H).

EXAMPLE 2

Preparation of

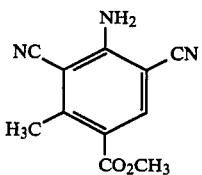

A solution of 28.1 ml of 37 percent strength aqueous formaldehyde in 25 ml of methanol is added dropwise at 0° C. to 43.5 g of methyl acetate, and a solution of 33 g of malodinitrile in 25 ml of methanol is then added. A solution of 28 g of triethylenediamine (1,4-diazabicyclo[2,2,2]octane) in 25 ml of methanol is added dropwise at 0° C. in the course of 1.5 hours. The mixture is stirred at 0° C. for a further 20 hours, and then refluxed for 7 hours under a reflux condenser. The mixture is cooled down, and the solids are filtered off with suction and washed with 20 ml of methanol. Yield: 16.2 g. $m_e+$: 215; melting point: 146° C.

EXAMPLE 3

Preparation of

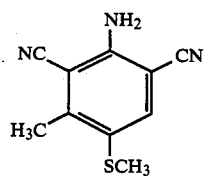

A solution of 18.8 ml of 37 percent strength aqueous formaldehyde in 25 ml of methanol, a solution of 33 g of malodinitrile in 50 ml of methanol, and a solution of 21.65 ml of morpholine in 25 ml of methanol are added dropwise in succession at 0° C. to 27.1 g of 96 percent strength 1-methylmercapto-2-propanone. The mixture is stirred at 0° C. for 5 hours and at room temperature for 48 hours, and 6.8 g of pale yellowish crystals having a melting point of 164° C. are then filtered off with suction.

$m_e+$: 203. The filtrate is heated at the boil for 5.5 hours. When it has cooled down, a further 6.7 g of 2,6-dicyano-3-methyl-4-methylmercaptoaniline are filtered off with suction.

EXAMPLE 4

Ethyl acetate is reacted in the manner of the method of Example 2 with acetaldehyde and malonitrile to give ethyl 2,6-dimethyl-3,5-dicyano-4-aminobenzoate. $m_e+$: 243; melting point 206° C.

EXAMPLE 5

Preparation of

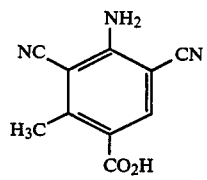

A suspension of 48.8 g of ethyl 2-methyl-3,5-dicyano-4-aminobenzoate in 300 ml of concentrated hydrochloric acid is refluxed for 20 hours. The solids are filtered off with suction, and washed with water until neutral. Yield: 36 g. The product can be further purified by dissolving it in dilute sodium hydroxide solution and precipitating with dilute hydrochloric acid.

IR: 2220 cm$^{-1}$(CN); melting point 300° C.
$^1$H-N.M.R. (DMSO-$d_6$/TMS); $\delta$=2.68 (s, 3H); 7.15 (s, 3H); 8.13 (s, 1H).

EXAMPLE 6

Preparation of

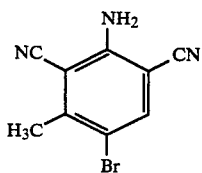

8 g of bromine are added dropwise at room temperature, with stirring, to a suspension of 10.05 g of 2-methyl-3,5-dicyano-4-aminobenzoic acid in 250 ml of concentrated hydrochloric acid, and a further 8 g of bromine are added after 48 hours. The mixture is stirred for a further 48 hours, and then heated at 50° C. for 3 hours. When the mixture has cooled down, 11.8 g of 2,6-dicyano-3-methyl-4-bromoaniline are filtered off with suction.

$m_e+$: 235 (100%), 237 (97%); melting point 212° C.

EXAMPLE 7

Preparation of the thioamide of the formula

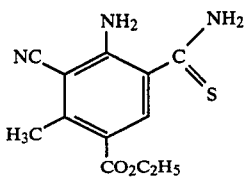

100 ml of 40 percent strength ammonium sulphide solution were added to a suspension of 18.3 g of ethyl 2-methyl-4-amino-3,5-dicyanobenzoate in 100 ml of methanol, and the mixture was stirred at 25° C. for 18 hours. The solids were filtered off with suction, and washed with water. Yield: 18.5 g, melting point 202° C. $M_e+$: 263 (67.5%).

EXAMPLE 8

Preparation of the benzisothiazole of the formula

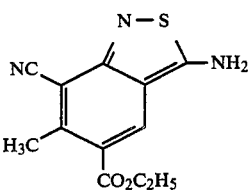

10.85 g of 35 percent strength hydrogen peroxide are added with stirring to a suspension of 18.4 g of ethyl 2-methyl-3-cyano-4-amino-5-thiocarboxamidobenzoate (or of isomeric ethyl 2-methyl-3-thiocarboxamido-4-amino-5-cyanobenzoate) in 75 ml of glacial acetic acid. The temperature rises up to 60° C., and the colour of the suspension changes to yellow. The mixture is stirred for 30 minutes, and the solids are filtered off with suction and washed with glacial acetic acid and water. Yield: 17.9 g (98% of theory)
$M_e+$: 261 (100%).

EXAMPLE 9

Preparation of the dyestuff of the formula

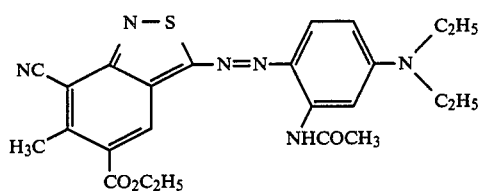

4.8 ml of 42 percent strength nitrosylsulphuric acid were added dropwise at 0° C. to a suspension of 7.57 g of 3-amino-5-carboethoxy-6-methyl-7-cyano-2,1-benzisothiazole in 40 ml of propionic acid and 80 ml of glacial acetic acid. The mixture was stirred at 0° C. for a further hour, and then clarified. The diazotisation solution was allowed to flow at 0° C. into a solution of 7.14 g of 3-diethylaminoacetanilide in 100 ml of glacial acetic acid and 20 ml of a 10 percent strength aminosulphonic acid solution. The mixture is stirred overnight and filtered with suction, and the filter cake is washed with water and dried. Yield: 12 g.

The dyestuff dyes polyester in a clear blue (Colour Index Hue Indication Chart No. 14) having good fastness properties, in particular fastness to light and sublimation. $\lambda_{max}$ (DMF): 620 nm.

The dyestuffs below can be obtained using an analogous or similar method.

| Example | X | Y | Z | K | Shade |
|---|---|---|---|---|---|
| 4 | CH₃ | CO₂C₂H₅ | H | ![structure: phenyl with N(C₂H₅)₂ and NHCOC₃H₇] | blue |
| 5 | " | " | " | ![structure: phenyl with N(C₃H₇)₂ and NHCOCH₃] | " |
| 6 | " | " | " | ![structure: phenyl with N(C₂H₅)₂] | " |
| 7 | " | " | " | ![structure: phenyl with N(C₂H₅)₂ and CH₃] | " |
| 8 | " | " | " | ![structure: phenyl with N(C₂H₄Cl)(C₂H₅) and CH₃] | " |
| 9 | " | CO₂CH₃ | " | ![structure: phenyl with CH(CH₃)-C(CH₃)₂-N-C₂H₄OCOCH₃] | " |
| 10 | " | CO₂C₂H₅ | CH₃ | ![structure: phenyl with N(C₂H₅)₂ and NHCOCH₃] | " |
| 11 | " | " | H | ![structure: naphthyl with NHC₂H₅] | " |
| 12 | " | " | " | ![structure: phenyl with OCH₃, N(C₂H₅)₂ and NHCOCH₃] | " |
| 13 | " | " | " | ![structure: phenyl with CH₃, NH—C₄H₉ and NHCOCH₃] | " |
| 14 | " | " | " | ![structure: phenyl with N(CH₂-phenyl)(C₂H₅) and CH₃] | " |

-continued

| Example | X | Y | Z | K | Shade |
|---|---|---|---|---|---|
| 15 | " | Br | " | 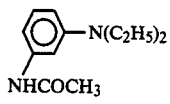 | " |
| 16 | " | " | " | 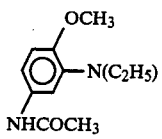 | " |
| 17 | " | SO₂CH₃ | " | 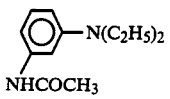 | " |
| 18 | " | " | " | 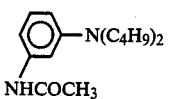 | " |
| 19 | " | SCH₃ | " | 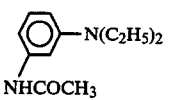 | " |
| 20 | " | " | " | 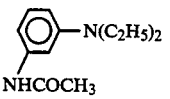 | " |

I claim:
1. A dyestuff of the formula

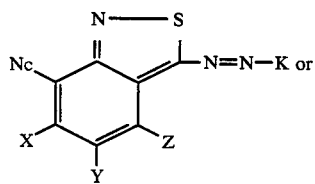 or

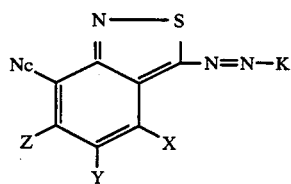

in which
K is the radical of a coupling component,
X is $C_{1-6}$-alkyl,
Y is $C_{1-6}$-alkyl-S—, $C_{1-6}$-alkyl-SO₂—, R—CO₂—, or bromine if Z=H,
Z is hydrogen or $C_{1-6}$-alkyl, and
R is $C_{1-6}$-alkyl, $C_{5-6}$-cycloalkyl or hydrogen.

2. A dyestuff according to claim 1, in which
X is methyl, and
Z is hydrogen.

3. A dystuff according to claim 1, in which

Y is $C_{1-6}$-alkyl—CO₂—.

4. A dyestuff according to claim 1, of the formula

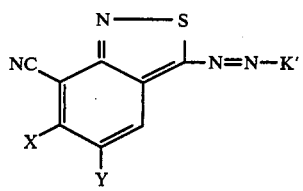

in which
K is a sulpho-free aminobenzene or aminonaphthalene coupling component.

5. A dyestuff according to claim 4, in which
K is a radical of the formula

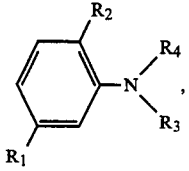

$R_1$ is hydrogen, CH₃, Cl, CF₃ or W—NH—,
W is HCO—, —CO-alkyl, —CO-phenyl, —CO₂-alkyl, —CO₂-phenyl, —SO₂-alkyl, —SO₂-phenyl or —PO(O-alkyl)₂,
$R_2$ is hydrogen, alkyl, —O-alkyl, O-phenyl, Cl or Br,
$R_3$ is hydrogen, alkyl, phenyl, or $C_{1-3}$-alkyl-phenyl, and
$R_4$ is hydrogen, alkyl or $C_{1-3}$-alkyl-phenyl, or together with $R_2$ forms a $C_3$-alkylene chain,
the foregoing alkyl radicals having 1–6 carbon atoms and being unsubstituted or substituted by OH, Cl, —O—$C_1$-$C_4$-alkyl, —O-phenyl, CN, —CO₂—$C_1$-$C_4$-alkyl or —OCO—NH—$C_1$-$C_4$-alkyl, the phenyl radicals being unsubstituted or substituted by Cl, CH₃, or $C_1$-$C_2$-alkoxy.

* * * * *

UNITED STATES PATENT AND TRADEMARK OFFICE
CERTIFICATE OF CORRECTION

PATENT NO. : 4,582,898
DATED : April 15, 1986
INVENTOR(S) : Rainer Hamprecht

It is certified that error appears in the above-identified patent and that said Letters Patent is hereby corrected as shown below:

Title Page, under "Foreign Application Priority Data"   Delete "1984" and substitute --1982--

Col. 1, line 29   Delete "amono" and substitute --amino--

Signed and Sealed this

Twenty-third Day of September 1986

[SEAL]

Attest:

Attesting Officer

DONALD J. QUIGG

Commissioner of Patents and Trademarks